United States Patent
Drapeau et al.

(10) Patent No.: US 8,882,506 B2
(45) Date of Patent: Nov. 11, 2014

(54) IMPLANT REPAIR SYSTEM AND METHOD (75) Inventors: Susan J. Drapeau, Cordova, TN (US); Daniel Andrew Shimko, Germantown, TN (US); Kelly Brook Emerton, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 65 days.

(21) Appl. No.: 12/857,683

(22) Filed: Aug. 17, 2010

(65) Prior Publication Data

US 2012/0045735 A1  Feb. 23, 2012

(51) Int. Cl.
| | | |
|---|---|---|
| *A61C 8/00* | (2006.01) | |
| *A61C 8/02* | (2006.01) | |
| *A61B 17/80* | (2006.01) | |
| *A61L 27/54* | (2006.01) | |
| *A61L 27/28* | (2006.01) | |
| *A61C 19/06* | (2006.01) | |
| *A61F 2/30* | (2006.01) | |
| *A61B 17/00* | (2006.01) | |
| *A61B 19/00* | (2006.01) | |

(52) U.S. Cl.
CPC .............. *A61C 19/06* (2013.01); *A61C 8/0006* (2013.01); *A61B 17/8085* (2013.01); *A61L 2300/414* (2013.01); *A61B 17/809* (2013.01); *A61L 27/54* (2013.01); *A61L 27/28* (2013.01); *A61B 2017/00004* (2013.01); *A61L 2430/12* (2013.01); *A61B 2019/5466* (2013.01); *A61F 2/30767* (2013.01)
USPC ......................................................... 433/172

(58) Field of Classification Search
CPC .... A61C 8/005; A61C 8/0012; A61C 8/0019; A61C 8/0022; A61C 8/0036; A61C 8/0048; A61C 8/0006; A61C 19/06; A61F 2/28; A61F 2/3099; A61B 17/8808; A61B 17/8085; A61B 2019/5466; A61B 17/809; A61B 2017/0004; A61L 27/28; A61L 27/54; A61L 2430/12; A61L 2300/414
USPC ......... 433/172–176, 201.1; 623/16.11, 17.17, 623/23.2
See application file for complete search history.

(56) References Cited

U.S. PATENT DOCUMENTS

| | | | | |
|---|---|---|---|---|
| 4,738,623 | A * | 4/1988 | Driskell | 433/173 |
| 5,051,091 | A * | 9/1991 | Rosenfeld | 433/201.1 |
| 5,372,503 | A * | 12/1994 | Elia | 433/215 |
| 5,511,565 | A * | 4/1996 | Syers | 128/898 |
| 6,171,106 | B1 * | 1/2001 | Kaneko et al. | 433/173 |
| 6,238,214 | B1 * | 5/2001 | Robinson | 433/215 |
| 6,250,922 | B1 | 6/2001 | Bassett et al. | |
| 6,312,258 | B1 * | 11/2001 | Ashman | 433/172 |
| 6,325,627 | B1 * | 12/2001 | Ashman | 433/173 |
| 6,413,089 | B1 * | 7/2002 | Ashman et al. | 433/174 |
| 6,497,573 | B2 | 12/2002 | Wagner et al. | |
| 6,722,884 | B2 * | 4/2004 | Ashman | 433/173 |
| 7,077,866 | B2 * | 7/2006 | Gresser et al. | 623/17.16 |
| 2001/0032022 | A1 * | 10/2001 | Ricci et al. | 623/23.56 |
| 2002/0009692 | A1 * | 1/2002 | Ashman | 433/173 |
| 2002/0055700 | A1 * | 5/2002 | Ashman | 602/41 |
| 2003/0027888 | A1 * | 2/2003 | Ashman | 523/120 |

(Continued)

*Primary Examiner* — Cris L Rodriguez
*Assistant Examiner* — Justin O'Donnell
(74) *Attorney, Agent, or Firm* — Sorell Lenna & Schmidt LLP (57) ABSTRACT

A dental implant system includes bone growth promoting material configured for disposal within a body cavity about an implant. A protective element is configured to overlay the bone growth promoting material. Methods of use are also disclosed.

19 Claims, 10 Drawing Sheets

(56) References Cited

U.S. PATENT DOCUMENTS

| | | |
|---|---|---|
| 2003/0087217 A1* | 5/2003 | Coatoam ................. 433/173 |
| 2003/0118968 A1* | 6/2003 | Massoud ................. 433/173 |
| 2004/0259056 A1* | 12/2004 | Holt ....................... 433/173 |
| 2005/0084820 A1* | 4/2005 | Ashman et al. ........... 433/173 |
| 2005/0192675 A1* | 9/2005 | Robinson ................ 623/23.46 |
| 2006/0008773 A1* | 1/2006 | Liao ....................... 433/173 |
| 2006/0265026 A1* | 11/2006 | Madjar et al. ............. 607/51 |
| 2007/0071735 A1* | 3/2007 | Elia ...................... 424/93.21 |
| 2007/0106398 A1* | 5/2007 | Steiner ................... 623/908 |
| 2008/0228279 A1* | 9/2008 | Hall ..................... 623/17.17 |
| 2008/0261178 A1 | 10/2008 | Homann et al. |
| 2008/0261179 A1 | 10/2008 | de Wild et al. |
| 2009/0061386 A1* | 3/2009 | Nishida ................. 433/173 |
| 2009/0061389 A1* | 3/2009 | Lomicka et al. ........ 433/201.1 |
| 2009/0192474 A1* | 7/2009 | Wei et al. ................ 604/285 |
| 2010/0003640 A1 | 1/2010 | Damstra et al. |
| 2010/0075278 A1 | 3/2010 | Fishell |
| 2010/0086897 A1 | 4/2010 | Schulz-Walz |
| 2010/0167239 A1 | 7/2010 | Guillard |

* cited by examiner

IMPLANT REPAIR SYSTEM AND METHOD

TECHNICAL FIELD

The present disclosure generally relates to medical devices for the treatment of bone disorders, for example, periodontal disorders, and more particularly to a dental implant repair system that employs bone growth material and includes a protective element to enhance treatment.

BACKGROUND

Implants are widely used in dental surgery for restoration of the jaw anatomy. Implants are employed, for example, to anchor a dental prosthesis such as, for example, an artificial tooth to a jawbone of a patient. Implants are secured in the bone by, for example, threaded fixation, press/friction fit, tapping, suturing and/or adhesive. Bone growth promoting material may be used and after a period of time, bone tissue can grow into the implant to ensure permanent fixation.

In some cases, however, the dental implant can suffer from bacterial invasion, loosening and/or improper implantation. These conditions can lead to peri-implantitis, bone loss and/or tissue loss, resulting in failure of the dental implant. As such, surgery may be required for treatment and replacement of the dental implant. This disclosure describes an improvement over these prior art technologies.

SUMMARY OF THE INVENTION

Accordingly, an implant repair system and method is provided for treating bone disorders, for example, periodontal disorders. It is contemplated that the implant repair system employs bone growth material and includes a protective element to enhance treatment. It is further contemplated that the protective element is disposed with a dental implant to protect underlying bone growth material from communication with an oral cavity and to prevent soft tissue collapse into a grafted region.

In one particular embodiment, in accordance with the principles of the present disclosure, a dental implant repair system is provided. The dental implant repair system includes bone growth promoting material configured for disposal within a body cavity about a dental implant. A protective element is configured to overlay the bone growth promoting material.

In one embodiment, a dental implant repair system is provided. The dental implant repair system includes bone growth promoting material configured for disposal within a body cavity disposed about a dental implant. A shield is configured to overlay the bone growth promoting material and prevent the bone growth promoting material from escaping the body cavity. An abutment is mounted with the dental implant in a configuration to retain the protective element with the dental implant.

In one embodiment, the dental implant repair system includes a bone growth promoting material configured for disposal within a body cavity disposed about a dental implant. A shield is provided having a substantially flat configuration and defining a first planar surface having a plurality of spikes extending therefrom, an opposing second surface and a central opening configured for disposal about the dental implant. The first planar surface engages the bone growth promoting material in a configuration to overlay and prevent the bone growth promoting material from escaping the body cavity. An abutment has a shaft configured for fixation with the dental implant and a head configured to engage and retain the shield with the dental implant. A prosthetic device is configured for mounting with the head of the abutment.

BRIEF DESCRIPTION OF THE DRAWINGS

The present disclosure will become more readily apparent from the specific description accompanied by the following drawings, in which.

DETAILED DESCRIPTION OF THE INVENTION

The exemplary embodiments of the implant repair system and related methods of use disclosed are discussed in terms of medical devices for the treatment of bone disorders, for example, periodontal disorders, and more particularly, in terms of a dental implant repair system that employs bone growth material and includes a protective element to enhance treatment. It is envisioned that the protective element is disposed with a dental implant to protect underlying bone growth material from communication with an oral cavity and to prevent soft tissue collapse into a grafted region. It is contemplated that the implant repair system and method is employed for repair treatment and to salvage an implant and/or prosthetic device implanted within a jaw and in jeopardy of implant failure. It is further contemplated that the implant system may be configured as a kit or system that includes one or a plurality of abutments, which may be variously sized and adapted, an implant and/or prosthetic device.

It is envisioned that the present disclosure may be employed to treat periodontal disorders such as, for example, peri-implantitis, chronic, aggressive and necrotizing periodontitis, gingivitis and other periodontal diseases. It is contemplated that the present disclosure may be employed with other osteal and bone related applications, including those associated with diagnostics and therapeutics. The present disclosure may also be alternatively employed with procedures for repairing vertebral implants. The system and methods of the present disclosure may also be used on animals, bone models and other non-living substrates, such as, for example, in training, testing and demonstration.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "superior" and "inferior" are relative and used only in the context to the other, and are not necessarily "upper" and "lower".

Figure 1:
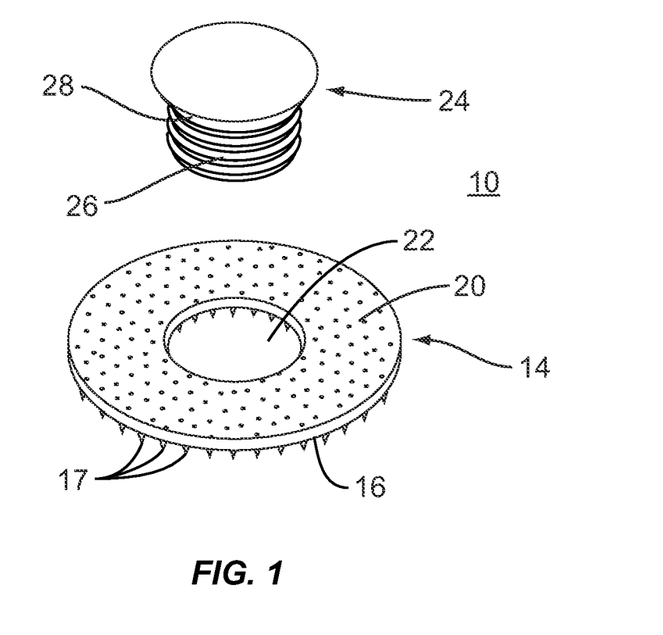
FIG. 1 is a perspective view of one particular embodiment of a dental implant repair system in accordance with the principles of the present disclosure.

The following discussion includes a description of an implant repair system and related methods of employing the implant repair system in accordance with the principles of the present disclosure. Alternate embodiments are also disclosed. Reference will now be made in detail to the exemplary embodiments of the present disclosure, which are illustrated in the accompanying figures. Turning now to FIG. 1, there is illustrated components of a dental implant repair system 10 in accordance with the principles of the present disclosure.

The components of the implant repair system are fabricated from materials suitable for medical applications, including metals, polymers, ceramics, biocompatible materials and/or their composites, depending on the particular application and/or preference of a medical practitioner. For example, the components of the implant repair system, individually or collectively, can be fabricated from materials such as stainless steel, titanium, thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, biocompatible materials such as polymers including plastics, metals, ceramics and composites thereof, rigid polymers including polyphenylene, polyamide, polyimide, polyetherimide, polyethylene, epoxy, and various components of the implant system, may have material composites, including the above materials, to achieve various desired characteristics such as strength, rigidity, elasticity, compliance, biomechanical performance, durability and radiolucency or imaging preference.

Implant repair system 10 is configured for treating dental implants in failure and/or those implants in jeopardy of failure, for example, dental implants suffering from bacterial invasion and resulting in peri-implantitis. The components of implant repair system 10 are configured to salvage a dental implant, which may include an abutment and/or prosthetic device, that has been implanted within a jaw.

Implant repair system 10 includes bone growth promoting material, such as, for example, bone graft 12 (FIG. 6) configured for disposal within a body cavity, such as, for example, a cavity in a jaw of a patient, which includes bone, cartilage or other tissues of the upper and lower jaw, gingiva, mandible and/or maxilla. The body cavity of the jaw is disposed about a dental implant, discussed below with regard to FIGS. 2-9, which was implanted within the jaw in a prior surgical procedure and suffers from failure or is in jeopardy of failure. It is envisioned that bone graft 12 is a particulate material which may include an osteoconductive material such as hydroxyapatite and/or osteoinductive agent such as a bone morphogenic protein to enhance bony fixation of the implant with the treated jaw area.

It is contemplated that bone graft 12 may include therapeutic polynucleotides or polypeptides, which can be packed or otherwise disposed in the body cavity of the jaw. It is further contemplated that bone graft 12 may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as hydroxyapatite, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, bone morphogenic protein (BMP), Growth and Differentiation Factors proteins (GDF) and cytokines.

Implant repair system 10 includes a protective element, such as, for example, a shield 14 having a substantially flat, disc configuration. Shield 14 is fabricated from a flexible, porous, resorbable material. It is contemplated that shield 14 may be fabricated from a biodegradeable material that resorbs over time in vivo. Examples of such include, but are not limited to, polyglycolide, polylactide, polycaprolactone, poly (ethylene glycol), polyurethanes, polyfumarates, polyacrylamides, collagen, silk, polyamines, polysaccharides, tissue or tissue products, and copolymers and blends thereof. It is further contemplated that shield 14 can be adjusted and/or trimmed to the configuration and dimension requirements of a particular application.

Shield 14 includes a first planar surface 16, such as, for example, a lower surface thereof, which engages bone graft 12 in a configuration to overlay bone graft 12 and prevent bone graft 12 from escaping from the body cavity, which includes the dental implant. Surface 16 has engagement elements, such as, for example, spikes 17 extending therefrom that are configured to facilitate fixation of shield 14 with bone graft 12. It is envisioned that all or a portion of surface 16 may be variously configured such as, for example, with smooth, arcuate, undulating and/or textured features.

Shield 14 has a second surface 20, such as, for example, an upper surface thereof, which is oriented to face an opposing direction relative to lower surface 16. Second surface 20 is configured to engage soft tissue, such as, for example, gingival tissue to facilitate support of shield 14 with bone graft 12 and the body cavity. It is contemplated that surface 20 may be freely exposed to an oral cavity and not engage soft tissue. It is further contemplated that all or a portion of surface 20 may be variously configured such as, for example, with smooth, arcuate, undulating and/or textured features.

Shield 14 has a central opening 22. Central opening 22 is configured for disposal about a dental implant. It is contemplated that central opening 22 may have various configurations such as, for example, circular, oval, rectangular, polygonal, offset and/or staggered. It is further contemplated that shield 14 may include one or a plurality of openings 22.

Implant repair system 10 includes an abutment 24 that is configured to provide support and structure to extend a dental implant above the gumline of patient to connect with a prosthetic. Abutment 24 has a threaded shaft 26 configured for fixation with a threaded cavity 31 of the dental implant (FIG. 8) and a head 28 having a lower surface and a circumferential side surface configured to engage and retain shield 14 with the dental implant. That is, the diameter of the abutment head 28 is larger than the diameter of the aperture 22 so that the surfaces of head 28 engage shield 14 and are prevented from passing therethrough. The shaft 26, however, is able to pass through aperture 22 to engage the threaded cavity 31 of the implant. It is contemplated that shaft 26 may have alternate surface configurations, such as, for example, smooth, textured for friction fit, oversized for pressure fit and/or slotted for pin connection to facilitate fixation with a correspondingly configured cavity of the dental implant.

It is further contemplated that implant repair system 10 may include one or a plurality of abutments for use with variously sized implants as will be discussed below, or implant repair system 10 may be packaged as a system or kit that includes bone graft material 12 and shield 14 but does not include an abutment. In such an embodiment, the pre-existing abutment associated with the dental implant fixed within the jaw cavity can be employed to fix shield 14 with the dental implant. Prosthetic(s) may also be included in the system or kit. The components of implant repair system 10 can be made of radiolucent materials such as polymers. Radiomarkers may be included for identification under x-ray, fluoroscopy, CT or other imaging techniques.

In one embodiment, one or all of the components of implant repair system 10 may include voids and/or openings, for including therapeutic polynucleotides or polypeptides and bone growth promoting material, which can be packed or otherwise disposed therein. For example, such voids and/or openings may include at least one agent including biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as hydroxyapatite, calcium phosphate and calcium sulfite, biologically active agents, for example, biologically active agents coated onto the exterior of one or all of the components of implant repair system 10 and/or applied thereto for gradual release such as by blending in a bioresorbable polymer that releases the biologically active agent or agents in an appropriate time dependent fashion as the polymer degrades within the patient. Suitable biologically active agents include, for example, bone morphogenic protein (BMP) and cytokines.

One of all of the components of implant repair system 10 may include one or a plurality of agent reservoirs. The agent reservoirs can be configured as drug depots with medication for pain and may include antibiotics and/or therapeutics. It is envisioned that the agent reservoirs contains active agents and may include one or a plurality of therapeutic agents and/or pharmacological agents for release, including sustained release, to treat, for example, pain, inflammation and degeneration. The agents may include pharmacological agents, such as, for example, antibiotics, anti-inflammatory drugs including but not limited to steroids, anti-viral and anti-retroviral compounds, therapeutic proteins or peptides, therapeutic nucleic acids (as naked plasmid or a component of an integrating or non-integrating gene therapy vector system), and combinations thereof.

The agent may also include analgesics or anesthetics such as acetic acid derivatives, COX-2 selective inhibitors, COX-2 inhibitors, enolic acid derivatives, propionic acid derivatives, salicylic acid derivatives, opioids, opioid/nonopioid combination products, adjuvant analgesics, and general and regional/local anesthetics.

The agent may also include antibiotics such as, for example, amoxicillin, beta-lactamases, aminoglycosides, beta-lactam (glycopeptide), clindamycin, chloramphenicol, cephalosporins, ciprofloxacin, erythromycin, fluoroquinolones, macrolides, metronidazole, penicillins, quinolones, rapamycin, rifampin, streptomycin, sulfonamide, tetracyclines, trimethoprim, trimethoprim-sulfamthoxazole, and vancomycin.

The agent may also include immunosuppressives agents, such as, for example, steroids, cyclosporine, cyclosporine analogs, cyclophosphamide, methylprednisone, prednisone, azathioprine, FK-506, 15-deoxyspergualin, prednisolone, methotrexate, thalidomide, methoxsalen, rapamycin, leflunomide, mizoribine (bredinin™), brequinar, deoxyspergualin, and azaspirane (SKF 105685), Orthoclone OKT™ 3 (muromonab-CD3). Sandimmune™, Neoral™, Sangdya™ (cyclosporine), Prograf™ (FK506, tacrolimus), Cellcept™ (mycophenolate motefil, of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrxate), Oxsoralen-Ultra™ (methoxsalen) and Rapamuen™ (sirolimus).

Referring to FIGS. 2-9, in assembly, operation and use, the implant repair system 10 is employed with a surgical procedure for treating dental implants in failure and/or those implants in jeopardy of failure, for example, dental implants suffering from bacterial invasion and resulting in peri-implantitis, as discussed herein. The implant system may also be employed with other surgical procedures for treatment of other periodontal diseases and bone disorders such as disorders of the vertebral column.

Figure 2:
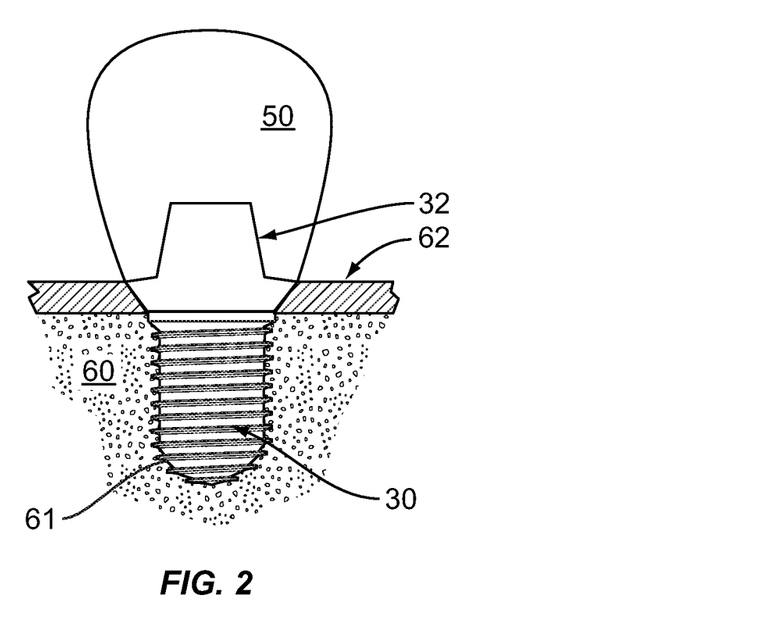
FIG. 2 is a side cross section view of a dental implant disposed within a healthy jaw cavity with an abutment and prosthetic attached thereto.

In connection with a prior implant procedure, a dental implant 30 is embedded in a body cavity of a jaw, such as, for example, a cavity 61 disposed in healthy gingival soft tissue 62 and bone 60 of the jaw such that the gingival soft tissue 62 of the gums overlies bone 60 of the jaw, as shown in FIG. 2. Cavity 61 is disposed circumferentially about dental implant 30. An implant abutment member 32 is removably engaged within threaded interior bore 31 in dental implant 30. A prosthetic device, such as, for example, a tooth crown 50 is affixed to the implant abutment member 32. Implant abutment member 32 comprises a head 70 including an upper surface 74 and a lower surface 76. Head 70 comprises a flange 78 positioned between surfaces 74, 76. Flange 78 includes a top surface 80 and a sidewall 82 connecting surface 80 and surface 76. An interface between surface 80 and sidewall 82 defines a sharp point 84.

Figure 3:
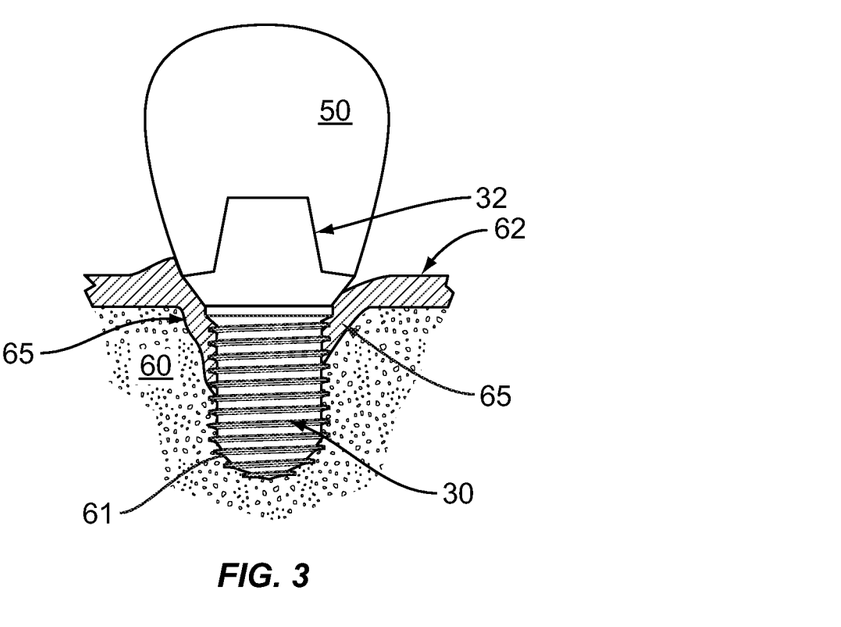
FIG. 3 is a side cross section view of the dental implant, abutment and prosthetic disposed within the jaw cavity shown in FIG. 2 having a disorder.

Subsequent to the implant procedure, as shown in FIG. 3, gingival swelling occurs and the area of bone 60 surrounding dental implant 30 includes an infected region 65 of peri-implantitis. An intrabony lesion has formed and soft-tissue swelling is present. Gingival soft tissue 62 recedes and erosion of bone 60 occurs due to the infection and results in loss of bony attachment and support for dental implant 30, leading to loosening and eventual removal of dental implant 30.

Figure 4:
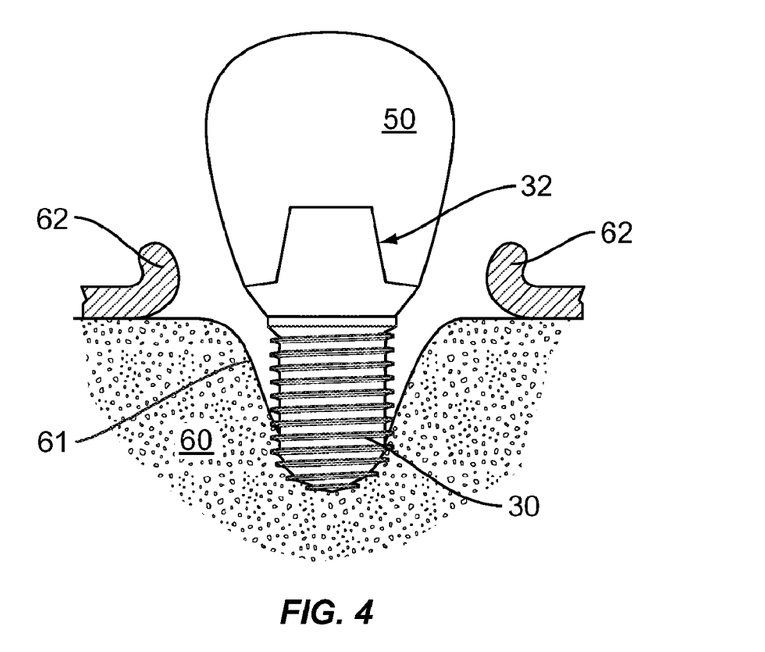
FIG. 4 is a side cross section view of the dental implant, abutment and prosthetic disposed within the jaw cavity shown in FIG. 3 showing treatment.
Figure 5:
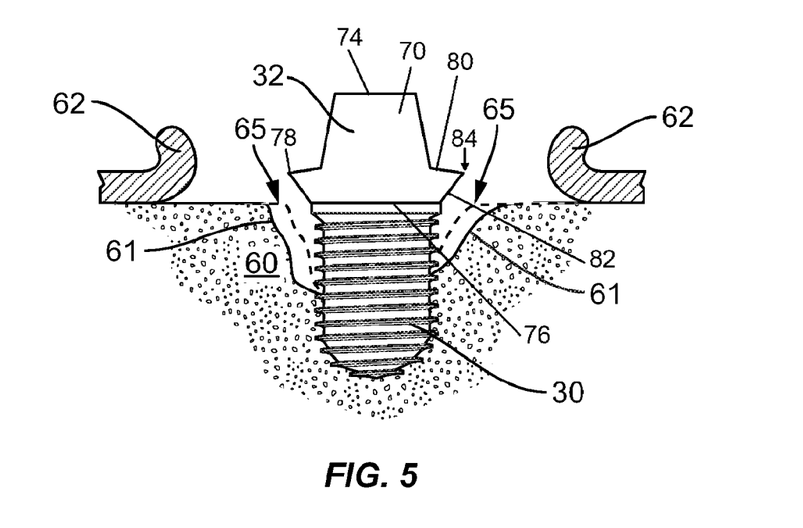
FIG. 5 is a side cross section view of the dental implant and abutment disposed within the jaw cavity shown in FIG. 4 showing treatment.

Dental implant repair system 10 is employed to salvage and/or repair dental implant 30 and the adjacent soft tissue and bone. As shown in FIG. 4, gingival soft tissue 62 is retracted from the implant region to expose cavity 61 and infected surface 65. Soft-tissue 62 has been reflected to expose the intrabony lesion. As shown in FIG. 5, crown 50 is removed and cavity 61 is mechanically debrided and the intrabony lesion has been forcibly debrided with an instrument (not shown) to remove infected surface 65 including granulation, tissue and bone matter. The surfaces of dental implant 30 are cleaned.

Figure 6:
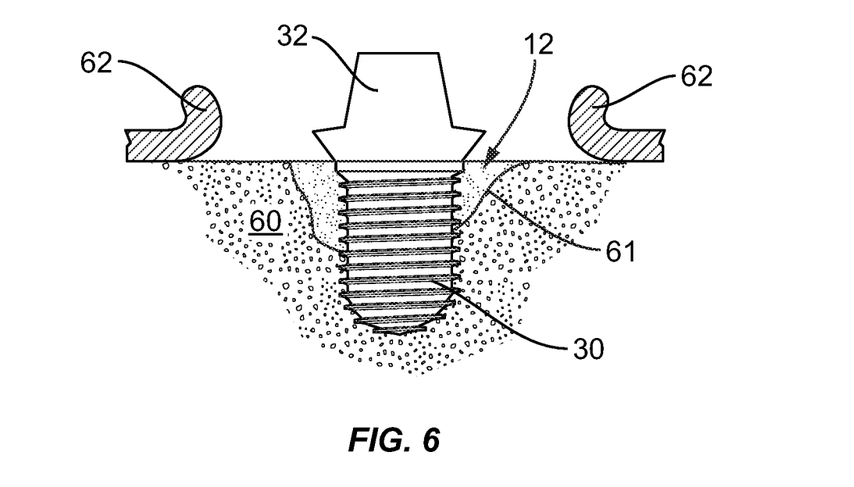
FIG. 6 is a side cross section view of the implant and abutment disposed within the jaw cavity shown in FIG. 5 showing treatment of an intrabony lesion with a bone grafting material of the dental implant repair system.
Figure 7:
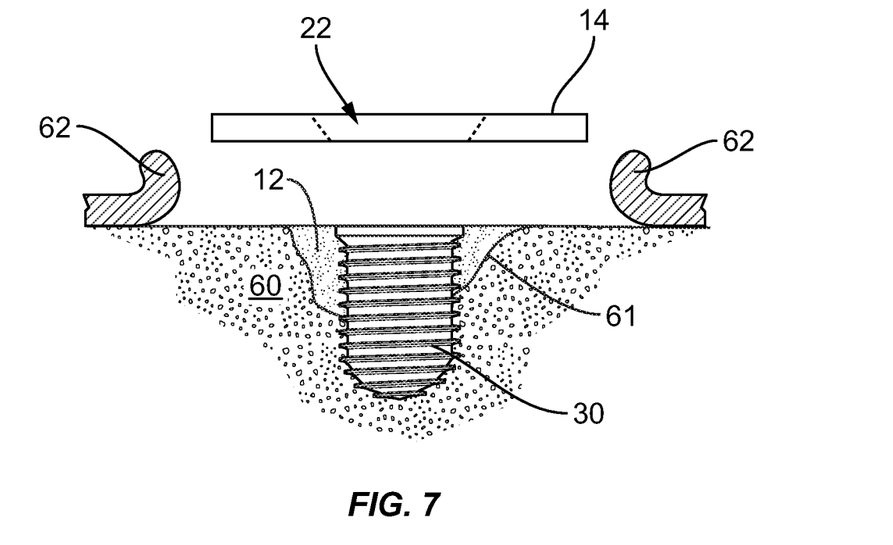
FIG. 7 is a side cross section view of the implant disposed within the jaw cavity shown in FIG. 6 showing placement of a shield.
Figure 8:
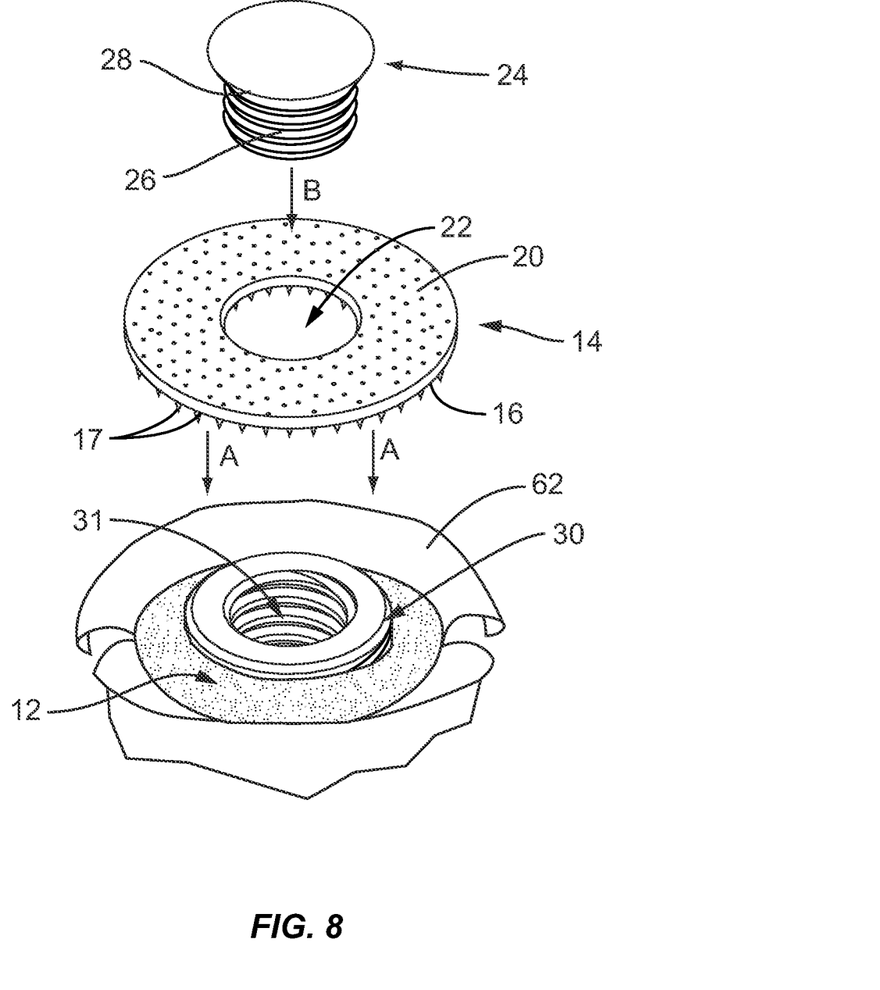
FIG. 8 is a perspective view of the implant disposed within the jaw cavity shown in FIG. 6 showing treatment with the dental implant repair system.

Referring to FIG. 6, bone graft 12 is injected and otherwise disposed within cavity 61 to surround and circumferentially dispose about dental implant 30 to reestablish integration. As shown in FIGS. 7-8, abutment member 32 is removed. Shield 14 is positioned over cavity 61 to overlay and engage bone graft 12, as shown by arrows A in FIG. 8, and prevent bone graft 12 from escaping from cavity 61. The outer portions of shield 14 overlay and engage gingival tissue. Central opening 22 is aligned with dental implant 30. Spikes 17 extend from surface 16 to facilitate fixation of shield 14 with bone graft 12. It is contemplated that shield 14 may be aligned with cavity 61 so as not to engage gingival tissue 62.

Figure 9:
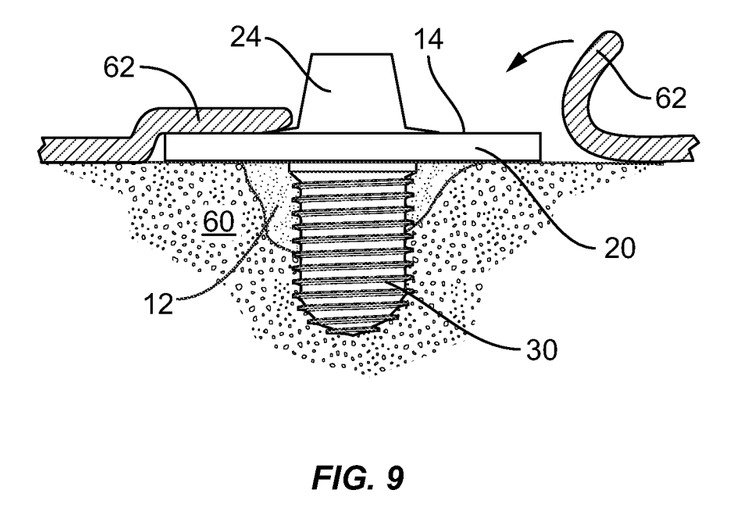
FIG. 9 is a side cross section view of the implant disposed with the jaw cavity shown in FIG. 6 showing treatment with the dental implant repair system wherein the shield has been placed and the soft-tissue is re-positioned to substantially cover the shield.

Abutment member 24 of dental implant repair system 10 is attached to dental implant 30 by disposing shaft 26 through central opening 22 and threading shaft 26 within bore 31, as shown by arrow B in FIG. 8. As shown in FIG. 9, the layers of gingival tissue 62 are returned to an orientation to overlie and engage surface 20 of shield 14, and side surfaces of shield 14. It is envisioned that dental implant repair system 10 provides sufficient stability to dental implant 30 such that subsequent procedures can be performed to attach a prosthetic to dental implant 30 and abutment 24. It is further contemplated that over time bone graft 12 becomes bone and shield 14 degrades.

Figure 10:
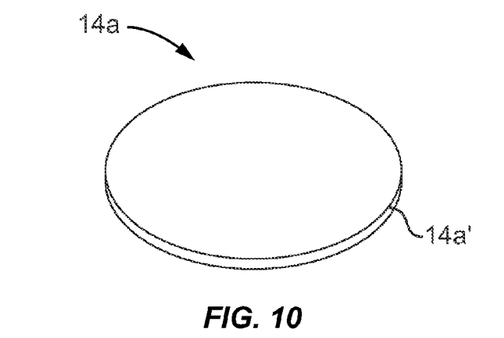
FIG. 10 is a perspective view of one embodiment of a protective element shown in FIG. 1.
Figure 10A:
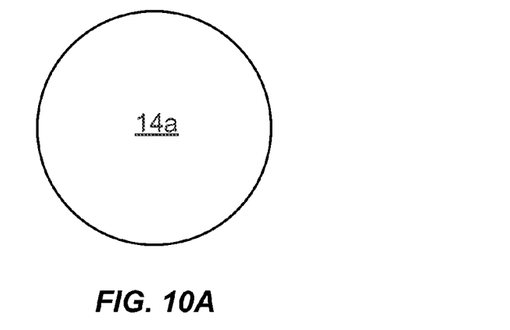
FIG. 10A is a plan view of the protective element shown in FIG. 10.

In one embodiment, as shown in FIGS. 10-10A, implant repair system 10, similar to that discussed above with regard to FIGS. 1-9, includes a shield 14a, similar to shield 14, which is a solid disc shaped member without an aperture and having a circular edge 14a' defining the periphery of two opposite flat surfaces. It is contemplated that shield 14a is provided with a full sheet such that a practitioner can modify the shield configuration according to a specific surgical application.

Figure 11:
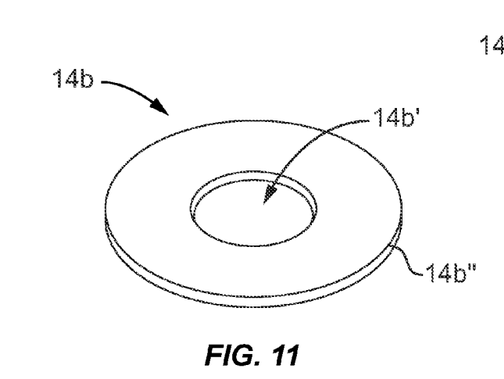
FIG. 11 is a perspective view of one embodiment of a protective element shown in FIG. 1.
Figure 11A:
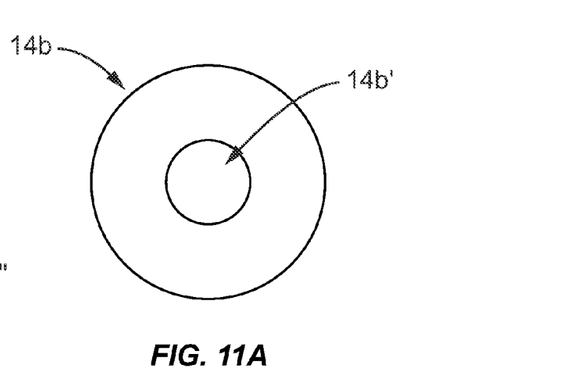
FIG. 11A is a plan view of the protective element shown in FIG. 11.
Figure 12:
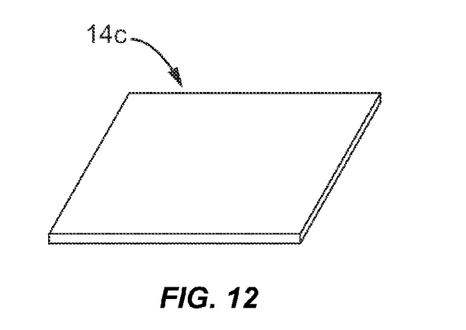
FIG. 12 is a perspective view of one embodiment of a protective element shown in FIG. 1.

In one embodiment, as shown in FIGS. 11-11A, implant repair system 10, similar to that discussed above, includes a shield 14b, similar to shield 14, which is a disc shaped member with an axial aperture 14b' and having a circular edge 14b" defining the outer periphery of two opposite flat surfaces. In one embodiment, as shown in FIG. 12, implant repair system 10, similar to that discussed above, includes a shield 14c, similar to shield 14, which is a solid four sided member without an aperture, and having a rectangular or square edge defining the outer periphery of two opposite flat surfaces.

Figure 13:
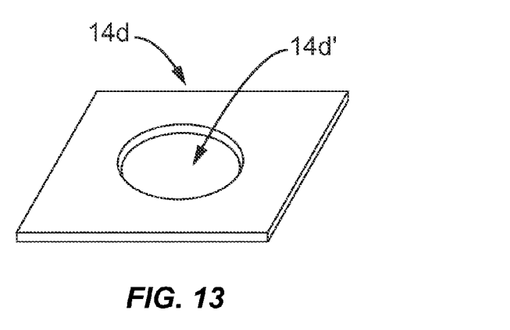
FIG. 13 is a perspective view of one embodiment of a protective element shown in FIG. 1.
Figure 14:
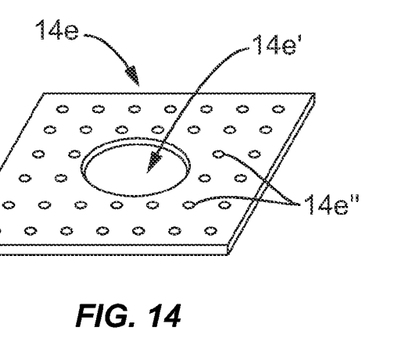
FIG. 14 is a perspective view of one embodiment of a protective element shown in FIG. 1.

In one embodiment, as shown in FIG. 13, implant repair system 10, similar to that discussed above, includes a shield 14d, similar to shield 14, which is a solid four sided member with an aperture 14d' and having a rectangular or square edge defining the outer periphery of two opposite flat surfaces. In one embodiment, as shown in FIG. 14, implant repair system 10, similar to that discussed above, includes a porous shield 14e having pores 14e", similar to shield 14, which is a four sided member with an aperture 14e', and having a rectangular or square edge defining the outer periphery of two opposite surfaces.

Figure 15:
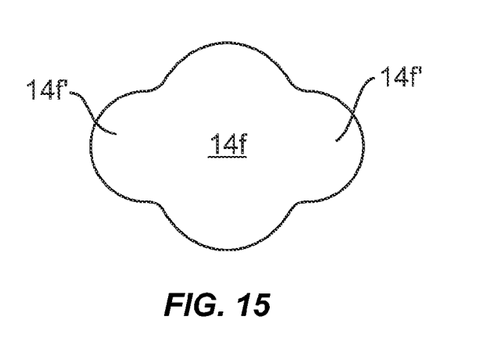
FIG. 15 is a plan view of one embodiment of a protective element shown in FIG. 1.
Figure 16:
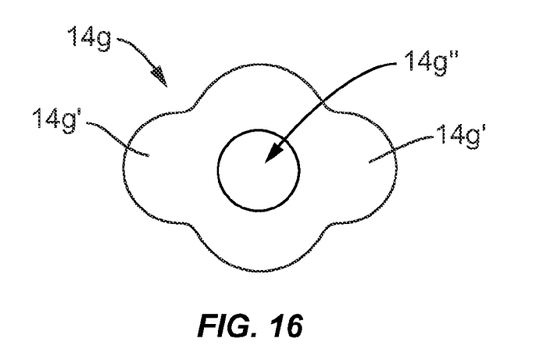
FIG. 16 is a plan view of one embodiment of a protective element shown in FIG. 1.
Figure 17:
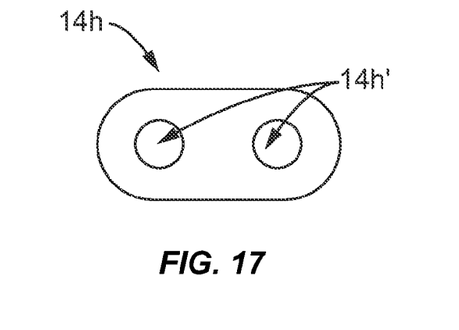
FIG. 17 is a plan view of one embodiment of a protective element shown in FIG. 1.

In one embodiment, as shown in FIG. 15, implant repair system 10, similar to that discussed above, includes a shield 14f, similar to shield 14, which is a solid, disc shaped member having oppositely extending convexities 14f'. In one embodiment, as shown in FIG. 16, implant repair system 10, similar to that discussed above, includes a shield 14g, similar to shield 14, which includes a solid, disc shaped member having oppositely extending convexities 14g' and a central aperture 14g". In one embodiment, as shown in FIG. 17, implant repair system 10, similar to that discussed above, includes a shield 14h, similar to shield 14, which is oblong in shape and includes two or more apertures 14h'.

Figure 18:
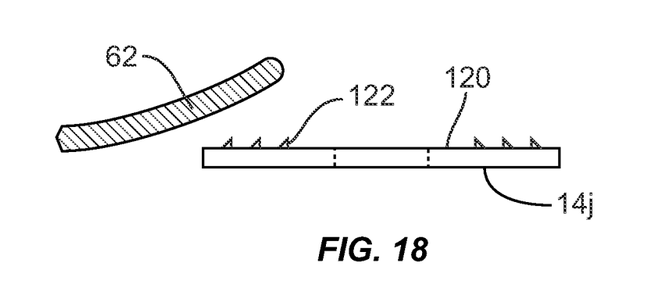
FIG. 18 is a side view of one embodiment of a protective element shown in FIG. 1 with gingival tissue.

In one embodiment, as shown in FIG. 18, implant repair system 10, similar to that discussed above, includes a shield 14j, similar to shield 14, having an upper surface 120. Upper surface 120 includes a plurality of barbs 122 extending therefrom configured to engage gingival tissue 62 to facilitate engagement of shield 14j with gingival tissue 62.

Figure 19:
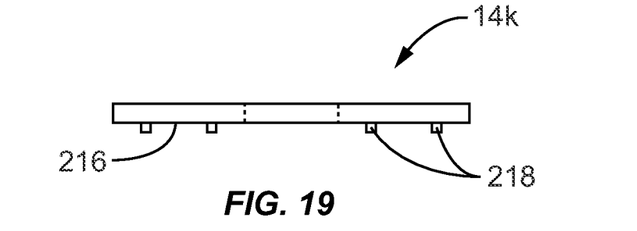
FIG. 19 is a side view of one embodiment of a protective element shown in FIG. 1.
Figure 20:
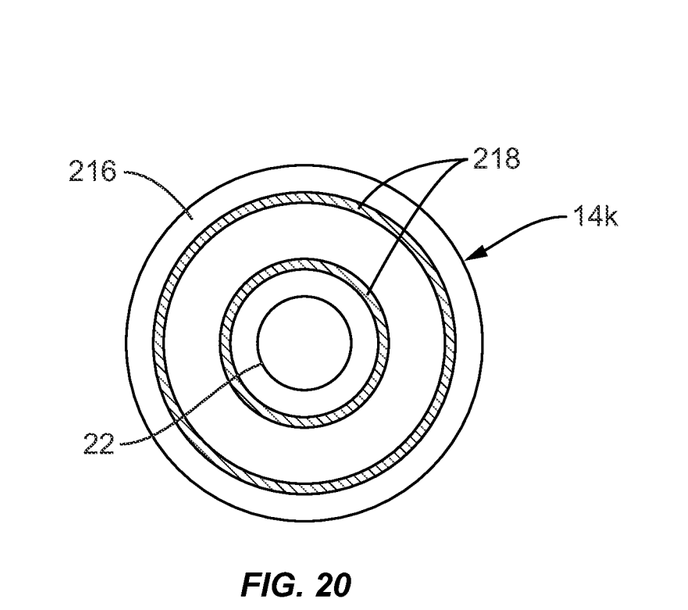
FIG. 20 is a plan view of the protective element shown in FIG. 19.

In one embodiment, as shown in FIGS. 19-20, implant repair system 10, similar to that discussed above, includes shield 14k, similar to shield 14, having a lower surface 216. Lower surface 216 defines a plurality of concentric protrusions 218 extending therefrom to facilitate engagement of shield 14 with bone graft 12.

Figure 21:
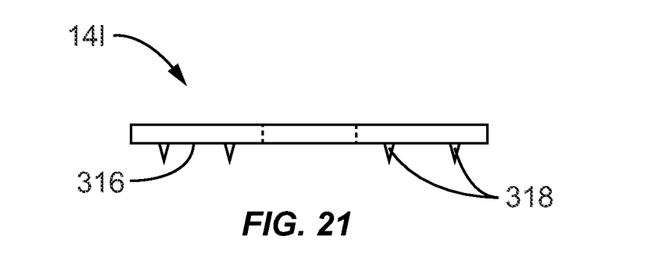
FIG. 21 is a side view of one embodiment of a protective element shown in FIG. 1.
Figure 22:
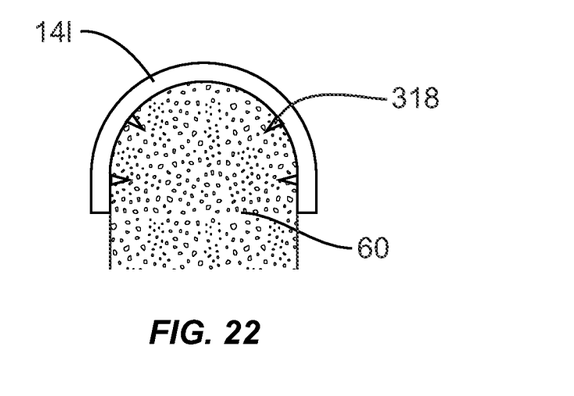
FIG. 22 is a side view of the protective element shown in FIG. 21 with a jaw in cross section wherein the shield is draped or shaped to conform to the surrounding region.
Figure 23:
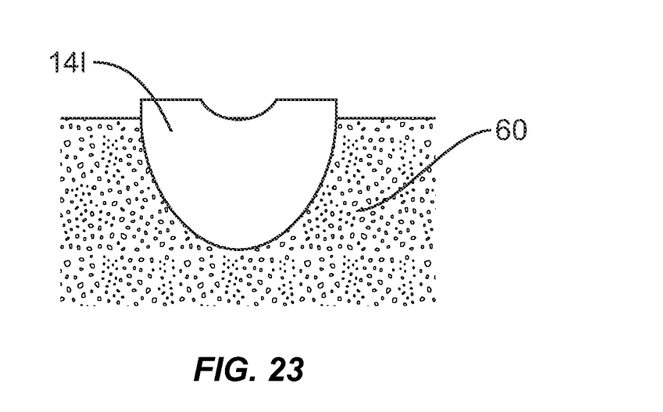
FIG. 23 is a schematic view of the protective element and a side view of the jaw shown in FIG. 21.

In one embodiment, as shown in FIGS. 21-23, implant repair system 10, similar to that discussed above, includes shield 14l, similar to shield 14, having a lower surface 316. Lower surface 316 includes a plurality of spikes 318 extending therefrom to facilitate engagement of shield 14 with bone graft 12 and adjacent soft tissues and bone 60. Spikes 318 stabilize shield 14, which is draped over the bony anatomy. It is contemplated that the bony region surrounding the bony anatomy can be an edentulous ridge or tooth or tooth socket.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A dental implant repair system comprising:
a dental implant comprising a threaded outer surface;
bone growth promoting material configured for disposal within a body cavity about said dental implant;
a protective element configured to overlay the bone growth promoting material, said protective element being porous, flexible and resorbable and defining a first planar surface configured to be in engagement with the bone growth material and a second opposing planar surface configured to engage gingival tissue, the protective element comprising an inner surface defining a central opening that tapers continuously from said second planar surface to said first planar surface;
an abutment having a threaded shaft and a head having an upper surface, a lower surface, an outwardly extending flange between said upper and lower surfaces and a circumferential side surface between said flange and said upper surface, said flange being continuously tapered, said shaft engaging a threaded recess of said implant such that said abutment is spaced apart from said threaded outer surface, said flange configured for disposal within said opening to retain the protective element with said implant and
a prosthetic device that removably engages said head.

2. A dental implant repair system according to claim 1, wherein the first planar surface engages the bone growth promoting material in a configuration to prevent graft from escaping the body cavity.

3. A dental implant repair system according to claim 1, wherein the second opposing planar surface includes a plurality of barbs extending therefrom configured to engage gingival tissue, said barbs each extending at an acute angle relative to said second opposing planar surface.

4. A dental implant repair system according to claim 1, wherein the first planar surface includes a plurality of engagement members extending therefrom, said engagement members being spikes each having a pointed end.

5. A dental implant repair system according to claim 1, wherein the first planar surface includes a plurality of concentric protrusions extending therefrom, said protrusions each having a cylindrical configuration.

6. A dental implant repair system according to claim 5, wherein each concentric protrusion of the plurality of concentric protrusions defines a circular wall.

7. A dental implant repair system according to claim 1, wherein said protective element includes a first pair of oppositely extending convexities disposed in a first axis and a second pair of oppositely extending convexities disposed in a second axis, perpendicular to the first axis, the first and second axes intersecting at a center of the central opening.

8. A dental implant repair system according to claim 1, further comprising agent reservoirs comprising at least one agent disposed therein, the agent being selected from a group consisting of antibiotics and anti-inflammatory drugs.

9. A dental implant repair system according to claim 1, wherein said abutment defines a longitudinal axis and said flange comprises a top surface that extends at an acute angle relative to said longitudinal axis.

10. A dental implant repair system according to claim 9, wherein said flange comprises a sidewall extending transverse to said longitudinal axis between said top surface and said lower surface, an interface between said top surface and said sidewall defining a sharp point.

11. A dental implant repair system according to claim 1, wherein said abutment defines a longitudinal axis and said lower surface extends perpendicular to said longitudinal axis.

12. A dental implant repair system comprising:
a dental implant comprising a threaded outer surface;
bone growth promoting material configured for disposal within a body cavity disposed about said dental implant;
a shield having an aperture, said shield configured to overlay the bone growth promoting material and prevent the bone growth promoting material from escaping the body cavity, said shield being porous, flexible and resorbable, said shield defining a first planar surface configured to be in engagement with the bone growth material and a second opposing planar surface configured to engage gingival tissue, said aperture being continuously tapered from said second planar surface to said first planar surface;
an abutment having a threaded shaft and a head having an upper surface, a lower surface, an outwardly extending flange between said upper and lower surfaces and a circumferential side surface between said flange and said upper surface, said flange being continuously tapered between said upper and lower surfaces and having a maximum diameter larger than that of said aperture of said shield, said shaft extending through said aperture and engaging a threaded recess of said implant such that said abutment is spaced apart from said threaded outer surface, and said flange being disposed within said aperture to retain the shield with the dental implant; and
a tooth crown that removably engages said head,
wherein at least one of the shield and abutment are coated with biologically active agents for time release of the biologically active agents within the patient.

13. A dental implant repair system according to claim 12, wherein the shield aperture defines a central opening disposed about the dental implant.

14. A dental implant repair system according to claim 13, wherein the first planar surface includes a plurality of spikes extending therefrom, said spikes being permanently fixed relative to said first planar surface.

15. A dental implant repair system according to claim 13, wherein the first planar surface includes a plurality of concentric protrusions extending therefrom.

16. A dental implant repair system according to claim 15, wherein each concentric protrusion of the plurality of concentric protrusions defines a circular wall.

17. A dental implant repair system according to claim 12, wherein the coating comprises a bioresorbable polymer containing the biologically active agents that releases the active agents as the bioresorbable polymer degrades over time.

18. A dental implant repair system according to claim 12, wherein the biologically active agents are selected from the group consisting of bone morphogenic protein (BMP) and cytokines.

19. A dental implant repair system comprising:
bone growth promoting material configured for disposal within a body cavity;
a dental implant having a threaded interior bore and a threaded outer surface, said bone growth promoting material being disposed about said dental implant;
a shield having a substantially flat configuration and defining a first planar surface having a plurality of spikes extending therefrom, an opposing second planar surface and a central opening configured for disposal about the dental implant, said opening being continuously tapered from said second planar surface to said first planar surface, the first planar surface engaging the bone growth promoting material in a configuration to overlay and prevent the bone growth promoting material from escaping the body cavity, said shield being porous, flexible and resorbable, and said second surface configured to engage gingival tissue;

an abutment having a threaded shaft that mates with the threaded interior bore to fix said abutment to said dental implant such that said abutment is spaced apart from said threaded outer surface, said abutment including a head having an upper surface, a lower surface, an outwardly extending flange between said upper and lower surfaces that is continuously tapered between said upper and lower surfaces and a circumferential side surface between said flange and said upper surface, said flange being disposed in said opening to retain the shield with the dental implant; and a prosthetic device mounted with the head of the abutment, wherein at least one of the shield and abutment are coated with biologically active agents for time release of the biologically active agents within the patient.

* * * * *